(12) United States Patent
Dolente et al.

(10) Patent No.: US 12,344,613 B2
(45) Date of Patent: Jul. 1, 2025

(54) EGFR INHIBITOR FOR THE TREATMENT OF CANCER

(71) Applicant: Hoffmann-La Roche Inc., Little Falls, NJ (US)

(72) Inventors: Cosimo Dolente, Allschwil (CH); Annick Goergler, Colmar (FR); David Hewings, Basel (CH); Georg Jaeschke, Basel (CH); Bernd Kuhn, Reinach (CH); Yvonne Alice Nagel, Basel (CH); Christa Ulrike Obst-Sander, Reinach BL (CH); Antonio Ricci, Biel-Benken (CH); Daniel Rueher, Raedersdorf (FR); Sandra Steiner, Sursee (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 763 days.

(21) Appl. No.: 17/620,239

(22) PCT Filed: Jun. 19, 2020

(86) PCT No.: PCT/EP2020/067076
§ 371 (c)(1),
(2) Date: Dec. 17, 2021

(87) PCT Pub. No.: WO2020/254562
PCT Pub. Date: Dec. 24, 2020

(65) Prior Publication Data
US 2022/0315592 A1 Oct. 6, 2022

(30) Foreign Application Priority Data
Jun. 21, 2019 (EP) .................................. 19181754

(51) Int. Cl.
| C07D 487/04 | (2006.01) |
| A61K 9/08 | (2006.01) |
| A61K 9/20 | (2006.01) |
| A61K 9/48 | (2006.01) |
| A61K 47/10 | (2017.01) |
| A61K 47/12 | (2006.01) |
| C07D 519/00 | (2006.01) |

(52) U.S. Cl.
CPC .............. *C07D 487/04* (2013.01); *A61K 9/08* (2013.01); *A61K 9/2013* (2013.01); *A61K 9/2018* (2013.01); *A61K 9/2054* (2013.01); *A61K 9/485* (2013.01); *A61K 9/4858* (2013.01); *A61K 9/4866* (2013.01); *A61K 47/10* (2013.01); *A61K 47/12* (2013.01); *C07D 519/00* (2013.01)

(58) Field of Classification Search
CPC ........................ C07D 487/04; C07D 519/00
See application file for complete search history.

(56) References Cited

U.S. PATENT DOCUMENTS

| 10,882,848 | B2 | 1/2021 | Duplessis et al. |
| 11,117,890 | B2 | 9/2021 | Jaeschke et al. |
| 11,708,354 | B2 | 7/2023 | Duplessis et al. |
| 12,209,091 | B2 | 1/2025 | Duplessis et al. |
| 2021/0079005 | A1 | 3/2021 | Duplessis et al. |
| 2022/0112199 | A1 | 4/2022 | Dolente et al. |
| 2022/0135571 | A1 | 5/2022 | Dolente et al. |
| 2022/0315577 | A1 | 10/2022 | Jaeschke et al. |
| 2022/0315591 | A1 | 10/2022 | Dolente et al. |
| 2022/0315593 | A1 | 10/2022 | Dolente et al. |
| 2023/0034696 | A1 | 2/2023 | Jaeschke et al. |
| 2023/0054473 | A1 | 2/2023 | Dolente et al. |
| 2023/0057891 | A1 | 2/2023 | Hewings et al. |
| 2024/0002390 | A1 | 1/2024 | Dolente et al. |

(Continued)

FOREIGN PATENT DOCUMENTS

| CL | 2021-03373 | 10/2022 |
| JP | 2021-529775 A | 11/2021 |
| JP | 2022-537191 A | 8/2022 |

(Continued)

OTHER PUBLICATIONS

"International Preliminary Report on Patentability—PCT/EP2020/067076" (Report Issuance Date: Dec. 21, 2021; Chapter I), :pp. 1-8 (Dec. 30, 2021).
"International Search Report—PCT/EP2020/067076" (w/Written Opinion), :pp. 1-15 (Jul. 28, 2020).
Jia, Y., et al., "Overcoming EGFR(T790M) and EGFR(C797S) resistance with mutant-selective allosteric inhibitors" Nature 534(7605):129-132 (May 25, 2016).

(Continued)

*Primary Examiner* — Susanna Moore

(57) ABSTRACT

The application relates to a compound of formula (I) containing a thiazole ring, an indazol ring and a 6,7-dihydro-5H-pyrrolo[1,2-c]imidazole ring system, to pharmaceutical compositions containing it and its medical use. The compounds are described as selective allosteric inhibitors of T790M/L858R, T790M/L858R/C797S, L858R, L858R/C797S containing EGFR mutants and thus useful for the treatment of cancer, in particular non-small cell lung cancer.

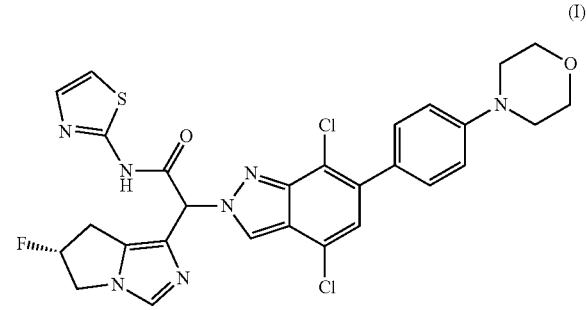

(I)

10 Claims, No Drawings

(56) References Cited

U.S. PATENT DOCUMENTS

| | | |
|---|---|---|
| 2024/0018154 A1 | 1/2024 | Dolente et al. |
| 2024/0059692 A1 | 2/2024 | Dolente et al. |

FOREIGN PATENT DOCUMENTS

| | | |
|---|---|---|
| JP | 2022-537769 A | 8/2022 |
| JP | 2022-537771 A | 8/2022 |
| JP | 2022-537772 A | 8/2022 |
| JP | 2022-538055 A | 8/2022 |
| JP | 7411588 B2 | 12/2023 |
| TW | 201834651 A | 10/2018 |
| WO | 2014/135876 | 9/2014 |
| WO | 2018/115218 A1 | 6/2018 |
| WO | 2018/220149 A1 | 12/2018 |
| WO | 2020/002487 A1 | 1/2020 |
| WO | 2020/254544 A1 | 12/2020 |
| WO | 2020/254546 A1 | 12/2020 |
| WO | 2020/254547 A1 | 12/2020 |
| WO | 2020/254565 A1 | 12/2020 |
| WO | 2020/254568 A1 | 12/2020 |
| WO | 2021/123084 A1 | 6/2021 |
| WO | 2021/123087 A1 | 6/2021 |
| WO | 2023/217923 A1 | 11/2023 |
| WO | 2023/217924 A1 | 11/2023 |

OTHER PUBLICATIONS

Bastin, R., et al., "Salt Selection and Optimisation Procedures for Pharmaceutical New Chemical Entities" Org Proc Res Dev 2000 4(5):427-435 (Jul. 19, 2000).

Kholodov, LE et al. Medicine "Clinical pharmacokinetics" (English translation), Moscow::pp. 83-98, 134-138, 160, 378-380 (1985).

Kummerer, K., "Pharmaceuticals in the Environment" Ann Rev Environ Res 35:57-75 (Nov. 1, 2010).

M. Small medical encyclopedia "Medicine" (No English translation), Russia: vol. 5:90-96 (1996).

Sergeev, P.V. Concise Course in Molecular Pharmacology (English translation), Moscow:Ministry of Health of the Russian Federation,:10 (1975).

EGFR INHIBITOR FOR THE TREATMENT OF CANCER

CROSS-REFERENCE TO RELATED APPLICATIONS

This application is a National Stage Entry under 35 U.S.C. § 371 of International Application No. PCT/EP2020/067076, filed Jun. 19, 2020, which claims benefit of priority to European Application No. 19181754.3 filed Jun. 21, 2019, each of which is incorporated herein by reference in its entirety.

The present invention provides a compound which is a selective allosteric inhibitor of T790M/L858R, T790M/L858R/C797S, L858R, L858R/C797S containing EGFR mutants, its manufacture, pharmaceutical compositions containing it and its use as therapeutically active substance.

The present invention provides a novel compound of formula (I)

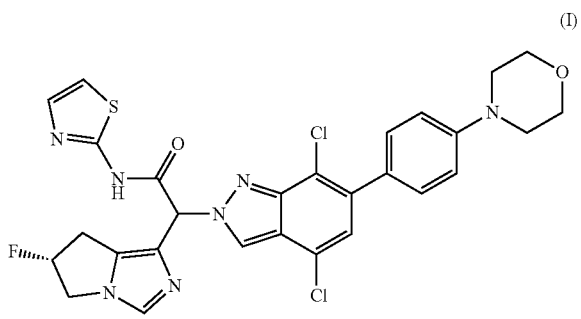 [SMILES: O=C(Nc1nccs1)C(c1ncn2c1C[C@@H](F)C2)n1cc2c(Cl)cc(-c3ccc(N4CCOCC4)cc3)c(Cl)c2n1]

or pharmaceutically acceptable salts.

The HER family receptor tyrosine kinases are mediators of cell growth, differentiation and survival. The receptor family includes four distinct members, i.e. epidermal growth factor receptor (EGFR, ErbB1, or HER1) HER2(ErbB2), HER3 (ErbB3) and HER4 (ErbB4). Upon ligand binding the receptors form homo and heterodimers and subsequent activation of the intrinsic tyrosine kinase activity leads to receptor auto-phosphorylation and the activation of downstream signaling molecules (Yarden, Y., Sliwkowski, M X. Untangling the ErbB signalling network. Nature Review Mol Cell Biol. 2001 February; 2(2): 127-37). De-regulation of EGFR by overexpression or mutation has been implicated in many types of human cancer including colorectal, pancreatic, gliomas, head and neck and lung cancer, in particular non-small cell lung cancer (NSCLC) and several EGFR targeting agents have been developed over the years (Ciardiello, F., and Tortora, G. (2008). EGFR antagonists in cancer treatment. The New England journal of medicine 358, 1160-1174). Erlotinib (Tarceva®), a reversible inhibitor of the EGFR tyrosine kinase was approved in numerous countries for the treatment of recurrent NSCLC.

An impressive single agent activity of EGFR tyrosine kinase inhibitors is observed in a subset of NSCLC patients whose tumors harbor somatic kinase domain mutations, whereas clinical benefit in wild-type EGFR patients is greatly diminished (Paez, J. et al. (2004). EGFR mutations in lung cancer: correlation with clinical response to gefitinib therapy. Science (New York, NY 304, 1497-1500). The most common somatic mutations of EGFR are exon 19 deletions with delta 746-750 the most prevalent mutation and the exon 21 amino acid substitutions with L858R the most frequent mutation (Sharma S V, Bell D W, Settleman J, Haber D A. Epidermal growth factor receptor mutations in lung cancer. Nat Rev Cancer. 2007 March; 7(3): 169-81).

Treatment resistance arises frequently, often due to the secondary T790M mutation within the ATP site of the receptor. Some developed mutant-selective irreversible inhibitors are highly active against the T790M mutant, but their efficacy can be compromised by acquired mutation of C797S, that is the cysteine residue with which they form a key covalent bond (Thress, K. S. et al. Acquired EGFR C797S mutation mediates resistance to AZD9291 in non-small cell lung cancer harboring EGFR T790M. Nat. Med. 21, 560-562 (2015)). C797S mutation was further reported by Wang to be a major mechanism for resistance to T790M-targeting EGFR inhibitors (Wang et al. *EGFR* C797S mutation mediates resistance to third-generation inhibitors in T790M-positive non-small cell lung cancer, J Hematol Oncol. 2016; 9: 59). Additional mutations that cause resistance to Osimertinib are described by Yang, for example L718Q. (Yang et al, Investigating Novel Resistance Mechanisms to Third-Generation EGFR Tyrosine Kinase Inhibitor Osimertinib in Non-Small Cell Lung Cancer Patients, Clinical Cancer Research, DOI: 10.1158/1078-0432.CCR-17-2310) Lu et al. (Targeting $EGFR^{L858R/T790M}$ and $EGFR^{L858R/T790M/C797S}$ resistance mutations in NSCLC: Current developments in medicinal chemistry, Med Res Rev 2018; 1-32) report in a review article on Targeting $EGFR^{L858R/T790M}$ and $EGFR^{L858R/T790M/WC797S}$ resistance mutations in NSCLC treatment.

As most available EGFR tyrosine kinase inhibitors target the ATP-site of the kinase, there is a need for new therapeutic agents that work differently, for example through targeting drug-resistant EGFR mutants.

Recent studies suggest that purposefully targeting allosteric sites might lead to mutant-selective inhibitors (Jia et al. Overcoming EGFR(T790M) and EGFR(C797S) resistance with mutant-selective allosteric inhibitors, June 2016, Nature 534, 129-132)

There is just a need in the generation of selective molecules that specifically inhibit T790M/L858R, T790M/L858R/C797S, L858R, L858R/C797S containing EGFR mutants useful for the therapeutic and/or prophylactic treatment of cancer, in particular T790M and C797S containing EGFR mutants.

WO2009158369 describes certain heterocyclic antibacterial agents. WO2016183534 describes certain heterocyclic compounds suitable as EBNA1 inhibitors. WO2011128279 describes certain heterocyclic compounds suitable as mGluR5 modulators.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compound of formula (I) are the hydrochloride salts, methanesulfonic acid salts and citric acid salts.

The abbreviation uM means microMolar and is equivalent to the symbol µM.

The abbreviation uL means microliter and is equivalent to the symbol µL.

The abbreviation ug means microgram and is equivalent to the symbol µg.

The compound of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention is a compound according to formula (I) as described herein and pharmaceutically acceptable salts thereof, more particularly a compound according to formula (I) as described herein.

Processes for the manufacture of a compound of formula (I) as described herein are also an object of the invention.

It will be appreciated that the compound of formula I in this invention may be derivatised at functional groups to provide derivatives which are capable of conversion back to the parent compound in vivo.

A certain embodiment of the invention relates to the compound of formula I as described herein, or a pharmaceutically acceptable salt thereof, for use as therapeutically active substance.

A certain embodiment of the invention relates to the compound of formula I as described herein, or a pharmaceutically acceptable salt thereof, for the use in the therapeutic and/or prophylactic treatment of cancer, in particular non-small-cell lung cancer.

A certain embodiment of the invention relates to the compound of formula I as described herein, or a pharmaceutically acceptable salt thereof, for the use in the therapeutic and/or prophylactic treatment of non-small-cell lung cancer.

A certain embodiment of the invention relates to the compound of formula I as described herein, or a pharmaceutically acceptable salt thereof, for the manufacture of a medicament for the therapeutic and/or prophylactic treatment of cancer, in particular non-small-cell lung cancer.

A certain embodiment of the invention relates to a pharmaceutical composition comprising the compound of formula I as described herein, or a pharmaceutically acceptable salt thereof, and a pharmaceutically acceptable auxiliary substance.

A certain embodiment of the invention relates to a method for the therapeutic and/or prophylactic treatment of cancer, in particular non-small-cell lung cancer by administering the compound of formula I as described herein, or a pharmaceutically acceptable salt thereof, to a patient.

A certain embodiment of the invention relates to the compound of formula I as described herein, or a pharmaceutically acceptable salt thereof, for the use as a medicament in therapeutic and/or prophylactic treatment of a patient with EGFR activating mutations suffering from cancer, in particular non-small-cell lung cancer, comprising determining the EGFR activating mutations status in said patient and then administering the compound of formula I as described herein, or a pharmaceutically acceptable salt thereof, to said patient.

A certain embodiment of the invention relates to the compound of formula I as described herein, or a pharmaceutically acceptable salt thereof, for the use as a medicament in therapeutic and/or prophylactic treatment of a patient with EGFR mutations T790M/L858R, T790M/L858R/C797S, L858R and/or L858R/C797S suffering from cancer, in particular non-small-cell lung cancer, comprising determining the EGFR activating mutations status in said patient and then administering the compound of formula I as described herein, or a pharmaceutically acceptable salt thereof, to said patient.

A certain embodiment of the invention relates to the compound of formula I as described herein, or a pharmaceutically acceptable salt thereof, for the use as a medicament in therapeutic and/or prophylactic treatment of a patient with EGFR activating mutations as determined with a Cobas® EGFR Mutation Test v2 suffering from cancer, in particular non-small-cell lung cancer, comprising determining the EGFR activating mutations status in said patient and then administering the compound of formula I as described herein, or a pharmaceutically acceptable salt thereof, to said patient.

Furthermore, the invention includes all substituents in its corresponding deuterated form, wherever applicable, of the compound of formula I.

The compound of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of the compound. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compound may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compound may be prepared by chirally selective synthesis or by separation of enantiomers. The separation of enantiomers may be carried out on the final product or alternatively on a suitable intermediate.

Also an embodiment of the present invention is a compound of formula (I) as described herein, when manufactured according to any one of the described processes.

Assay Procedures

HTRF Phospho EGFR TMLRCS Assay (Cellular)
Cell Line and Media

BaF3-TMLRCS cell line were obtained from Crownbio (San Diego, CA, USA). Cells were maintained at 37° C., 5% $CO_2$ in RPMI ATCC (Gibco 31870)+2 mM Glutamine+0.5 µg/ml Puromycin supplemented with 10% fetal bovine serum (FBS) (Gibco).

Protocol

Cells are transferred as above to Greiner Bio-One, Nr. 784-08 micro-titerplate at 20000 cells/well in 12.5 µl of growth medium/well after the plates had been pre-filled with 12.5 nl of DMSO solutions of the to be tested compounds (in dose response) or DMSO only. After spinning the plates at 300×g for 30 seconds the cells were incubated for 4 hours at 37 C, 5% CO2, 95% humidity. The cells were lysed by adding to the compound mix 4 µl/well of the supplemented lysis buffer (Cis-bio, Phospho-EGFR HTRF kit, 64EG1PEH), followed by incubation for 30 min at room temperature with shaking (400 rpm). The plates were then frozen and stored overnight at −80 C. On the next day and after thawing the plates, 4 µl of a mixture of anti-Phospho-EGFR Cryptate and of anti-Phospho-EGFR-d2 antibody solutions prepared in the supplied detection buffer was added to each well. The lidded plates were then incubated for 4 h at room temperature before reading the fluorescence emission at 616 and 665 nm using an Envision reader (Perkin Elmer). Data was analyzed in similar fashion as above using the normalized ratio of the 665 to 616 signals multiplied by 10000.

The results are shown in Table 1

| Example | $IC_{50}$ (−baF3) µM |
|---------|----------------------|
| 1       | 0.005                |

The compound of formula (I) and its pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compound of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

Preparation of Pharmaceutical Compositions Comprising the Compound of the Invention:

Tablets of the following composition are manufactured in the usual manner:

|                            | mg/tablet |     |     |     |
|----------------------------|-----------|-----|-----|-----|
| Ingredient                 | 5         | 25  | 100 | 500 |
| Compound of formula I      | 5         | 25  | 100 | 500 |
| Lactose Anhydrous DTG      | 125       | 105 | 30  | 150 |
| Sta-Rx 1500                | 6         | 6   | 6   | 60  |
| Microcrystalline Cellulose | 30        | 30  | 30  | 450 |
| Magnesium Stearate         | 1         | 1   | 1   | 1   |
| Total                      | 167       | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| Ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoapproximatively. The mixture is filled by machine into suitable capsules, e.g. hard gelatin capsules.

Injection solutions of the following composition are manufactured:

| Ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLE 1

2-[4,7-Dichloro-6-(4-morpholinophenyl)indazol-2-yl]-2-[(6R)-6-fluoro-6,7-dihydro-5H-pyrrolo[1,2-c]imidazol-1-yl]-N-thiazol-2-yl-acetamide

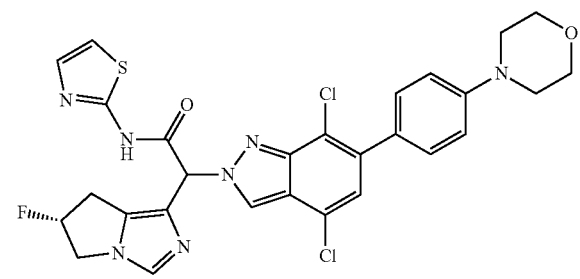 [SMILES: O=C(Nc1nccs1)C(c1ncn2c1C[C@@H](F)C2)n1cc2c(Cl)cc(-c3ccc(N4CCOCC4)cc3)c(Cl)c2n1]

Step 1: 4-Bromo-3,6-dichloro-2-fluorobenzaldehyde

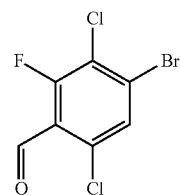 [SMILES: O=Cc1c(Cl)cc(Br)c(Cl)c1F]

A solution of 1-bromo-2,5-dichloro-3-fluorobenzene (9.41 g, 38.6 mmol) in tetrahydrofuran (70 ml) was cooled in a dry ice/acetone bath. LDA, 2 mol/1 in THF (21.2 ml, 42.5 mmol, 1.1 equiv.) was added and the mixture was stirred at −75° C. for 20 minutes. N,N-Dimethylformamide (2.82 g, 3.0 ml, 38.6 mmol, 1 equiv.) was added dropwise and stirred for 1 hour. A solution of acetic acid in ether (1:1, 10 ml) was added. The mixture was allowed to warm to room temperature. Water was added and the mixture was extracted with ethyl acetate. The organic layers were washed with water, dried (MgSO$_4$), filtered and concentrated in vacuo to give the crude title compound (quantitative yield) as light yellow solid. The compound was used for the next step without further purification.

Step 2: 6-Bromo-4,7-dichloro-1H-indazole

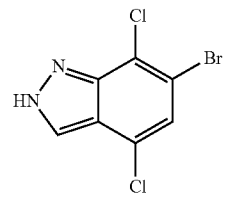 [SMILES: Clc1cc(Br)c(Cl)c2n[nH]cc12]

To a solution of 4-bromo-3,6-dichloro-2-fluorobenzaldehyde (Example 1, step 1) (10.5 g, 38.6 mmol) in dioxane (50 ml) was added hydrazine hydrate (3.86 g. 3.78 ml, 77.2 mmol, 2.0 equiv.). The mixture was stirred at room temperature for 3 days. Hydrazine hydrate (386 mg, 0.38 ml, 7.72 mmol, 0.2 equiv.) was added and the mixture was warmed to 70° C. for 7 hours. After cooling to room temperature water was added and the precipitated solid was collected by filtration. To the solid was added a small amount of acetonitrile and stirred for 2 hours. The solid was collected by filtration, washed with a small amount of acetonitrile and dried to give the title compound (7.8 g, 76% yield) as off-white solid. m/z 267.0/269.0, [M+H]$^+$, ESI pos, Br isotopes.

Step 3: Ethyl 2-(6-bromo-4,7-dichloro-indazol-2-yl)acetate

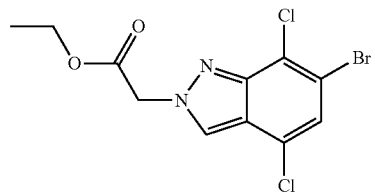 [SMILES: CCOC(=O)Cn1cc2c(Cl)cc(Br)c(Cl)c2n1]

To a solution of 6-bromo-4,7-dichloro-1H-indazole (Example 1, step 2) (7.84 g, 29.5 mmol, Eq: 1) in N,N-dimethylacetamide (11.5 mL) was added ethyl 2-bromoacetate (9.85 g, 6.53 ml, 59 mmol, 2.0 equiv.). The reaction mixture was stirred for 16 hours at 100° C. Ice was added and the precipitated solid was collected by filtration and washed with water. The compound was crystallized from boiling ethanol. The solid was collected by filtration, washed with a small amount of ethanol and dried to give the title compound as a white solid (7.5 g, 70% yield). m/z 353.0, 355.0, [M+H]+, ESI pos, Br isotopes.

Step 4: tert-Butyl (2S,4R)-2-[2-(6-bromo-4,7-dichloro-indazol-2-yl)-3-ethoxy-3-oxo-propanoyl]-4-fluoro-pyrrolidine-1-carboxylate

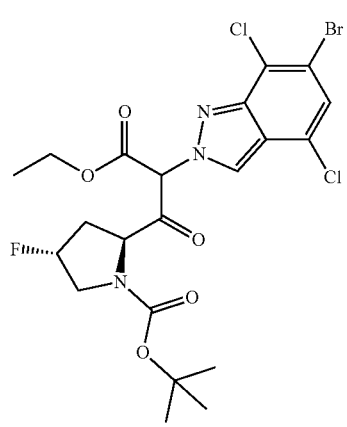 [SMILES: CCOC(=O)C(C(=O)[C@@H]1C[C@@H](F)CN1C(=O)OC(C)(C)C)n1cc2c(Cl)cc(Br)c(Cl)c2n1]

A solution of (2S,4R)-1-(tert-butoxycarbonyl)-4-fluoro-pyrrolidine-2-carboxylic acid (2.34 g, 10 mmol, 1.55 equiv.) in tetrahydrofuran (11 ml) was cooled in an ice bath. Carbonyldiimidazole (1.63 g, 10 mmol, 1.55 equiv.) was added. The cooling bath was removed and the mixture was stirred for 3 hours to give solution A. A solution of ethyl 2-(6-bromo-4,7-dichloro-indazol-2-yl)acetate (Example 1, step 3) (2.28 g, 6.5 mmol) in tetrahydrofuran (11 ml) was cooled to −70° C. LDA, 2 mol/l in tetrahydrofuran (5.0 ml, 10 mmol, 1.55 equiv.) was added dropwise within 5 min. The mixture was stirred for 30 minutes at −70° C. Solution A was added dropwise within 5 minutes. The mixture was allowed to warm to room temperature in the cooling bath overnight. After addition of saturated aqueous NH4Cl-solution, the mixture was extracted twice with ethyl acetate. The organic layers were washed with water, combined, dried over sodium sulphate and concentrated to dryness to give the crude title compound (quantitative yield) which was used for the next step without further purification. m/z 566.1/568.1, [M+H]+, ESI pos, Br isotopes.

Step 5: Ethyl 2-(6-bromo-4,7-dichloro-indazol-2-yl)-2-[(6R)-6-fluoro-3-thioxo-2,5,6,7-tetrahydropyrrolo[1,2-c]imidazol-1-yl]acetate

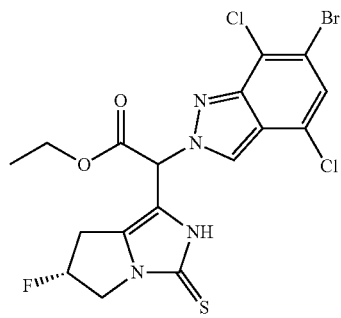 [SMILES: CCOC(=O)C(c1[nH]c(=S)n2c1C[C@@H](F)C2)n1cc2c(Cl)cc(Br)c(Cl)c2n1]

A solution of tert-butyl (2S,4R)-2-[2-(6-bromo-4,7-dichloro-indazol-2-yl)-3-ethoxy-3-oxo-propanoyl]-4-fluoro-pyrrolidine-1-carboxylate (Example 1, step 4) (4.23 g, 6.41 mmol) in HCl, 4M in dioxane (11 ml) was stirred for 1 hour at room temperature. The mixture was concentrated to dryness. The residue was dissolved in ethanol (37 ml), potassium thiocyanate (829 mg, 8.53 mmol, 1.33 equiv.) and HCl, 1 M in ethanol (12.8 ml) were added and stirred 40 hours at room temperature. Water was added and the mixture was extracted with ethyl acetate. The organic layers were washed with water, dried over MgSO4, filtered, concentrated and dried to give the crude title compound (2.5 g, 76% yield) which was used for the next step without further purification. m/z 509.0/511.0, [M+H]+, ESI pos, Br isotopes.

Step 6: Ethyl 2-(6-bromo-4,7-dichloro-indazol-2-yl)-2-[(6R)-6-fluoro-6,7-dihydro-5H-pyrrolo[1,2-c]imidazol-1-yl]acetate

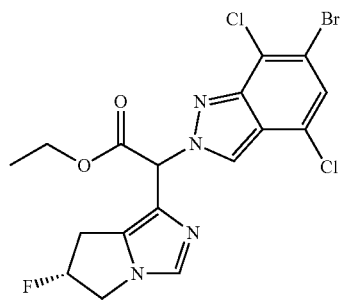 [SMILES: CCOC(=O)C(c1ncn2c1C[C@@H](F)C2)n1cc2c(Cl)cc(Br)c(Cl)c2n1]

A solution of ethyl 2-(6-bromo-4,7-dichloro-indazol-2-yl)-2-[(6R)-6-fluoro-3-thioxo-2,5,6,7-tetrahydropyrrolo[1,2-c]imidazol-1-yl]acetate (Example 1, step 5) (1.46 g, 2.88 mmol) in acetic acid (10 ml) was cooled to 10° C. Hydrogen peroxide, 35% (1.12 g, 1.01 ml, 11.5 mmol, 4 equiv.) was added dropwise. The reaction mixture was stirred for 1 hour at room temperature. The excess of hydrogen peroxide was destroyed by addition of saturated sodium sulfite solution. After addition of some water (just enough to dissolve all salts) and ethyl acetate the mixture was brought to pH 9 by careful addition of solid sodium carbonate. The mixture was extracted with ethyl acetate. The organic layers were washed with water, dried over sodium sulphate and concentrated. The product was purified by chromatography (SiO2, 0-100% ethyl acetate in heptane) to give the title compound (0.81 g, 58% yield) as light brown solid. m/z 475.0/477.0, [M+H]+, ESI pos, Br isotopes.

Step 7: Ethyl 2-[4,7-dichloro-6-(4-morpholinophenyl)indazol-2-yl]-2-[(6R)-6-fluoro-6,7-dihydro-5H-pyrrolo[1,2-c]imidazol-1-yl]acetate

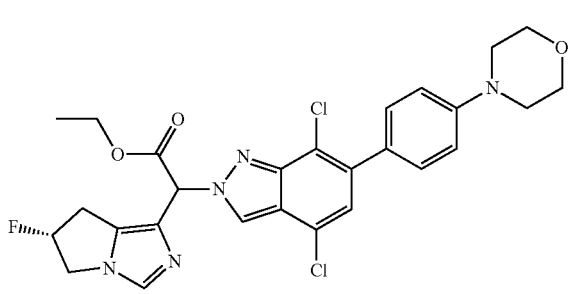 [SMILES: CCOC(=O)C(c1ncn2c1C[C@@H](F)C2)n1cc2c(Cl)cc(-c3ccc(N4CCOCC4)cc3)c(Cl)c2n1]

Ethyl 2-(6-bromo-4,7-dichloro-indazol-2-yl)-2-[(6R)-6-fluoro-6,7-dihydro-5H-pyrrolo[1,2-c]imidazol-1-yl]acetate (Example 1, step 6) (100 mg, 0.21 mmol), (4-morpholinophenyl)boronic acid (130 mg, 0.63 mmol, 3 equiv.) and cesium carbonate (205 mg, 0.63 mmol, 3 equiv.) were mixed with toluene (3.0 ml), degassed by bubbling argon through the mixture under ultra sonic treatment. [1,1'-Bis(diphenylphosphino)ferrocene]dichloropalladium(II) (15 mg, 0.02 mmol, 0.1 equiv.) was added and the mixture was stirred for 30 minutes at 110° C. in a sealed tube. The mixture was cooled to room temperature, diluted with ethyl acetate, washed with half concentrated sodium carbonate solution, dried over sodium sulphate and concentrated. The crude material was purified by flash chromatography (SiO2, 0% to 40% methanol in ethyl acetate) to give the title compound (82 mg, 69% yield) as light brown amorphous solid. m/z 558.4, [M+H]+, ESI pos.

Step 8: 2-[4,7-Dichloro-6-(4-morpholinophenyl)indazol-2-yl]-2-[(6R)-6-fluoro-6,7-dihydro-5H-pyrrolo[1,2-c]imidazol-1-yl]-N-thiazol-2-yl-acetamide

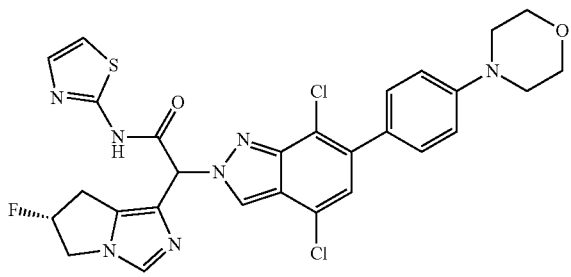 [SMILES: O=C(Nc1nccs1)C(c1ncn2c1C[C@@H](F)C2)n1cc2c(Cl)cc(-c3ccc(N4CCOCC4)cc3)c(Cl)c2n1]

To a solution of ethyl 2-[4,7-dichloro-6-(4-morpholinophenyl)indazol-2-yl]-2-[(6R)-6-fluoro-6,7-dihydro-5H-pyrrolo[1,2-c]imidazol-1-yl]acetate (Example 1, step 7) (40 mg, 0.071 mmol) in tetrahydrofuran (1.1 ml) were added LiOH 1M (101 µl, 0.10 mmol, 1.5 equiv.) and water (400 µl). The mixture was stirred for 30 minutes at room temperature. The residue was concentrated and dried. The residue was dissolved in N,N-dimethylformamide (1.1 ml). After addition of thiazol-2-amine (9 mg, 0.086 mmol, 1.2 equiv.), HATU (33 mg, 0.086 mmol, 1.2 equiv.) and Hunig's base (28 mg, 0.037 ml, 0.21 mmol, 3 equiv.) the mixture was stirred for 1 hour at room temperature. Water was added and the mixture was extracted with ethyl acetate. The organic layers were combined, dried with sodium sulfate, filtered and concentrated. The crude material was purified by flash chromatography (SiO2, 0% to 40% methanol in ethyl acetate) to give the title compound (22 mg, 50% yield) as light brown solid. m/z 612.4, [M+H]+, ESI pos.

The invention claimed is:

1. A compound or a pharmaceutically acceptable salt thereof of formula (I)

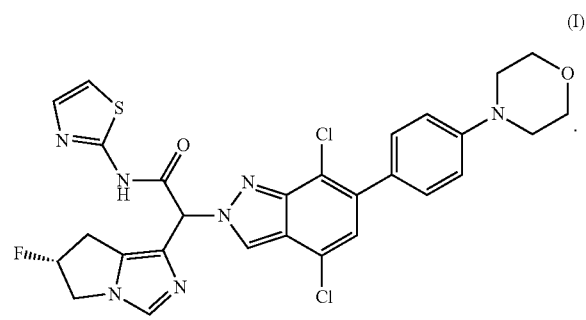 [SMILES: O=C(Nc1nccs1)C(c1ncn2c1C[C@@H](F)C2)n1cc2c(Cl)cc(-c3ccc(N4CCOCC4)cc3)c(Cl)c2n1]

(I)

2. A compound of formula (I)

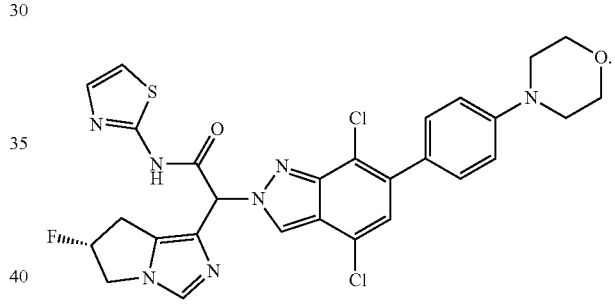

3. A pharmaceutical composition comprising the compound or pharmaceutically acceptable salt thereof of claim 1 and a therapeutically inert carrier.

4. A method for treating a cancer in a patient in need thereof, the method comprising administering an effective amount of the compound or pharmaceutically acceptable salt of claim 1 to the patient with cancer, wherein the cancer comprises one or more Epidermal Growth Factor Receptor (EGFR) mutations selected from T790M, L858R, and C797S.

5. A method for treating a non-small cell lung cancer (NSCLC) in a patient in need thereof, the method comprising administering an effective amount of the compound or pharmaceutically acceptable salt of claim 1 to the patient with NSCLC, wherein the NSCLC comprises one or more Epidermal Growth Factor Receptor (EGFR) mutations selected from T790M, L858R, and C797S.

6. A pharmaceutical composition comprising the compound of claim 2 and a therapeutically inert carrier.

7. A method for treating a cancer in a patient in need thereof, the method comprising administering an effective amount of the compound of claim 2 to the patient with cancer, wherein the cancer comprises one or more Epidermal Growth Factor Receptor (EGFR) mutations selected from T790M, L858R, and C797S.

8. A method for treating a non-small cell lung cancer (NSCLC) in a patient in need thereof, the method comprising administering an effective amount of the compound of claim 2 to the patient with NSCLC, wherein the NSCLC comprises one or more Epidermal Growth Factor Receptor (EGFR) mutations selected from T790M, L858R, and C797S.

9. The method according to claim 4, wherein the cancer comprises EGFR mutations at T790M/L858R, T790M/L858R/C797S, L858R, or L858R/C797S.

10. The method according to claim 5, wherein the NSCLC comprises EGFR mutations at T790M/L858R, T790M/L858R/C797S, L858R, or L858R/C797S.

* * * * *